United States Patent
Hingorani et al.

(10) Patent No.: US 10,092,672 B2
(45) Date of Patent: Oct. 9, 2018

(54) AIR FILTRATION MEDIA FOR AIR PURIFICATION

(71) Applicant: Lennox Industries Inc., Richardson, TX (US)

(72) Inventors: Sanjeev Hingorani, Richardson, TX (US); Thomas Wolowicz, Richardson, TX (US); Henry Greist, Richardson, TX (US)

(73) Assignee: Lennox Industries Inc., Richardson, TX (US)

( * ) Notice: Subject to any disclaimer, the term of this patent is extended or adjusted under 35 U.S.C. 154(b) by 3 days.

(21) Appl. No.: 15/296,147

(22) Filed: Oct. 18, 2016

(65) Prior Publication Data
US 2017/0035927 A1    Feb. 9, 2017

Related U.S. Application Data

(63) Continuation of application No. 13/919,383, filed on Jun. 17, 2013, now Pat. No. 9,498,555.

(51) Int. Cl.
| | | |
|---|---|---|
| A61L 9/20 | (2006.01) | |
| F24F 3/16 | (2006.01) | |
| B01D 46/00 | (2006.01) | |
| B01D 46/52 | (2006.01) | |
| B01D 53/00 | (2006.01) | |

(52) U.S. Cl.
CPC .......... *A61L 9/205* (2013.01); *B01D 46/0001* (2013.01); *B01D 46/0027* (2013.01); *B01D 46/522* (2013.01); *B01D 53/007* (2013.01); *F24F 3/1603* (2013.01); *A61L 2209/14* (2013.01); *B01D 2239/065* (2013.01); *B01D 2255/802* (2013.01); *B01D 2275/10* (2013.01); *B01D 2279/50* (2013.01); *F24F 2003/1628* (2013.01); *F24F 2003/1667* (2013.01); *Y10T 29/49885* (2015.01)

(58) Field of Classification Search
CPC ... A61L 9/205; B01D 46/0001; B01D 53/007; B01D 46/522; B01D 46/0027; F24F 3/1603
See application file for complete search history.

(56) References Cited

U.S. PATENT DOCUMENTS

| | | | |
|---|---|---|---|
| 5,766,455 | A | 6/1998 | Berman et al. |
| 5,919,422 | A | 7/1999 | Yamanaka et al. |
| 7,740,810 | B2 | 6/2010 | Hay et al. |
| 8,328,917 | B2 | 12/2012 | Garfield et al. |
| 2006/0228275 | A1 | 10/2006 | Rutman et al. |
| 2006/0277877 | A1 | 12/2006 | Shields |
| 2006/0278075 | A1 | 12/2006 | Blackner |
| 2007/0207186 | A1* | 9/2007 | Scanlon ............. A61F 2/07 424/424 |
| 2009/0095160 | A1 | 4/2009 | Troxell et al. |
| 2010/0247404 | A1 | 9/2010 | Ptak et al. |

\* cited by examiner

*Primary Examiner* — Regina M Yoo
(74) *Attorney, Agent, or Firm* — Winstead PC

(57) ABSTRACT

An air filtration media for use with a heating ventilation and air condition (HVAC) system is provided. The filtration media comprises an air filter media layer having a first and second side, a PCO media layer having a first and second side, and a barrier layer positioned between the second side of the air filter media layer and the first side of the PCO media layer. The air filter media layer, barrier layer, and PCO layer are pleated together and enclosed within a frame for placement adjacent a light source within a plenum of the HVAC system.

16 Claims, 3 Drawing Sheets

AIR FILTRATION MEDIA FOR AIR PURIFICATION

CROSS-REFERENCED APPLICATIONS

This application is a continuation of U.S. patent application Ser. No. 13/919,383 filed on Jun. 17, 2013. U.S. patent application Ser. No. 13/919,383 is incorporated herein by reference.

TECHNICAL FIELD

The present disclosure is directed, in general, to air filtration and purification for heating ventilation and air conditioning (HVAC) systems and, more particularly, to a photocatalytic oxidation (PCO) air filtration media for air purification.

BACKGROUND

Indoor air can include trace amounts of contaminants: e.g., dust, smoke, carbon monoxide, as well as volatile organic compounds generated or outgassed from the living space as a byproduct of our modern building methods. As indoor air flows through the return ducts of a heating, ventilation and air conditioning (HVAC) system, the air first encounters a system air filter which blocks the passage of particulate contaminants, and allows the return air to enter the portion of the HVAC system where it is heated, cooled, humidified, or dehumidified.

While filters are essential in removing particulate contaminants from the air prior to conditioning, they only block the passage of some particulate contaminants but do not destroy them. As a result, some air filtration and purification systems utilize ultraviolet (UV) radiation in combination with air filters in HVAC systems to further kill airborne bacteria and viruses. Photocatalytic oxidation (PCO) air purification systems employ a photocatalytic coating, such as titanium dioxide, inter alia, in combination with an activating photonic light source of a particular wavelength to destroy indoor airborne contaminants including volatile organic compounds such as formaldehyde, toluene, propanol, butene, and acetaldehyde. The system arrangement commonly includes one or more ultraviolet lamps, and a photocatalytic monolith, such as a honeycomb, coated with the photocatalytic coating. Titanium dioxide, e.g., is well known as a photocatalyst in a fluid purifier to destroy such contaminants.

SUMMARY

The present disclosure provides, in one aspect, an air filtration media for use with a heating ventilation and air condition (HVAC) system is disclosed. The filtration media comprises an air filter media layer having a first and second side; and a PCO media layer having a first and second side. A barrier layer is positioned between the second side of the air filter media layer and the first side of the PCO media layer. The air filter media layer, barrier layer, and PCO layer may be pleated together and enclosed within a frame for placement adjacent a light source within a plenum of the HVAC system. In some embodiments, the light source may comprise an ultraviolet lamp and the PCO layer may comprise either titanium dioxide or other photoreactive metal semiconductor material.

In another aspect, a method of manufacturing an air purification system for use in plenum comprising a heating, ventilation and air condition (HVAC) system is provided. The method comprises providing an air filter media having a first side and a second side; and providing a PCO media having a first side and a second side. The method further comprises positioning a protective barrier between the second side of the air filter media and the first side of the PCO media; and pleating the air filter media, barrier, and PCO media into at least one pleating pattern having multiple pleats and enclosing the at least one pleating pattern within a frame. Next a light source is provided and positioned adjacent the frame proximal to the second side of the PCO media, wherein the frame and light source are positionable within the plenum of the HVAC system. In some embodiments, the barrier layer may be a laminate coated onto the second side of the air filter media. In another embodiment, the barrier layer may be a laminate coated onto the first side of the PCO media.

In yet another aspect a heating, ventilating and air conditioning (HVAC) air purification system, the air purification system comprising a filtration media, the filtration media enclosed within a frame. The filtration media comprises an air filter layer having a first and second side; a photocatalytic oxidation (PCO) layer having a first and second side; and a barrier layer between the second side of the air filter layer and the first side of the PCO layer. An ultraviolet light source is adjacent to the filtration media proximal to the second side of the PCO layer, wherein the filtration media and light source are situated within a plenum.

The foregoing has outlined features of the present disclosure so that those skilled in the pertinent art may better understand the detailed. Additional features of the disclosure will be described hereinafter that form the subject of the claims. Those skilled in the pertinent art should appreciate that they can readily use the disclosed conception and specific embodiment as a basis for designing or modifying other structures for carrying out the same purposes of the present disclosure. Those skilled in the pertinent art should also realize that such equivalent constructions do not depart from the spirit and scope of the present disclosure.

BRIEF DESCRIPTION OF THE DRAWINGS

For a more complete understanding of the disclosure, reference is now made to the following descriptions taken in conjunction with the accompanying drawing, in which.

DETAILED DESCRIPTION

Ultraviolet (UV) lamps in PCO air purification applications generally emit ultraviolet-wavelength photons within 360° around the longitudinal axis of the lamps. While UV light is extremely useful in the air purification and PCO applications, UV light is also harmful to certain materials commonly found in the HVAC system, such as the air filter. Exposure of UV radiation results in early degradation and decreased system performance.

Traditional air filtration and purification systems require a certain amount of plenum and/or cabinet space to provide enough clearance within the cabinet for all of the components configured sequentially, the components including an air filtration media, one or more protective reflectors/light barriers, a light source, and a PCO media. These PCO systems not only require an additional amount of clearance to accommodate the spacing of the components but also can increase installation and maintenance costs since each component may be installed and maintained separately. Certain UV bulbs are available which incorporate the reflector/barrier and the light source as one component, which may simplify the maintenance and installation, but comprise a higher component cost than traditional lamps without reflectors.

Accordingly, the present disclosure provides a heating, ventilation, and air conditioning (HVAC) air purification system that incorporates the air filtration media, protective barrier/reflector and PCO media into a single, more compact filtration media that protects the air filter media from UV light and photocatalytic oxidation, while not interfering in the air purification and PCO applications. An air purification system utilizes the new air filtration media, the media enclosed in a frame and comprising an air filter layer and a PCO layer positioned on opposing sides of a barrier layer. Air flow enters through the air filter layer and out from the PCO layer, wherein a light source, such as a UV light source, is positioned outside of the frame proximate to the PCO layer. The PCO layer and UV light source work together to destroy particulate contaminates. The barrier layer protects the air filter layer from damage and destruction by the UV light source. Previous PCO purification systems have heretofore been unable to combine the separate filter media with the PCO media because of the damaging effects of UV light on traditional filter media. Further, the combination of the two separate media would be counterintuitive because of various cost and physical limitations in pleating PCO media, the lack of a protective barrier, and previous design considerations utilizing the light source before the PCO media such that air flows through the UV light prior to encountering the PCO media.

Figure 1:
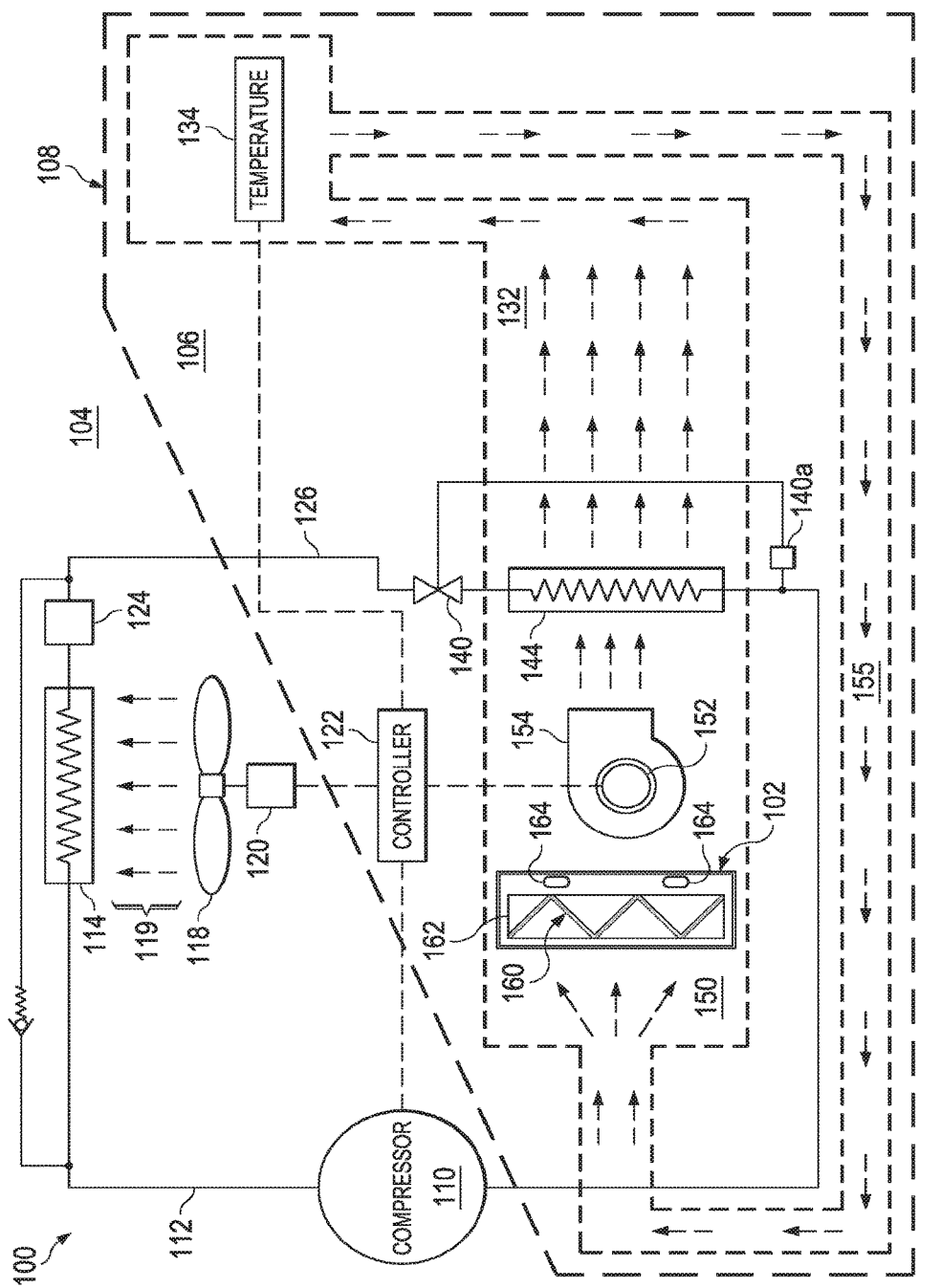
FIG. 1 is a schematic view of a conventional heating, ventilation and air conditioning (HVAC) system having a photocatalytic oxidation (PCO) subsystem and constructed according to the principles of the present disclosure.

Referring initially to FIG. 1, illustrated is a schematic view of a conventional heating, ventilation and air conditioning (HVAC) system 100 having an air purification subsystem 102 and constructed according to the principles of the present disclosure. The HVAC system 100 comprises an outdoor portion 104, i.e., above line 108, and an indoor portion 106, i.e., below line 108. The outdoor portion 104 comprises a conventional electric motor-driven compressor 110 connected via a conduit 112 to a heat exchanger 114 disposed outdoors, typically, and comprising a refrigerant fluid primary condenser. In the embodiment illustrated in FIG. 1, heat exchange between refrigerant fluid flowing through the condenser heat exchanger 114 and ambient air is controlled by a fan 118 having plural fixed-pitch blades and which is driven by a variable speed electric motor 120. The electric motor 120 may be an electrically-commutated type operating on variable frequency and voltage AC electric power as supplied to the motor via a controller 122. Fan 118 propels a heat exchange medium, such as ambient outdoor air 119, through the condenser heat exchanger 116. The condenser heat exchanger 116 may also operate with other forms of heat exchange media at controlled flow rates thereof. Control of heat exchange medium 119 flowing over condenser heat exchanger 116 may take other forms such as a constant speed variable pitch fan, air flow control louvers, or control of a variable flow of a liquid heat exchange medium. The condenser heat exchanger 116 is also operably connected to a conventional refrigerant fluid filter and dryer 124 disposed in a conduit 126 for conducting condensed refrigerant fluid to a conventional refrigerant fluid expansion device 140. A temperature sensor 134, disposed within a conditioned space 132 to be conditioned by the system 100, is also operably connected to the controller 122. Controlled/conditioned space 132, as well as a return air path 155 from space 132, is represented schematically in the drawing figures.

The indoor portion 106 comprises the controller 122, a heat exchanger plenum 150, the air purification subsystem 102, a drive motor 152, a motor-driven blower 154, the refrigerant fluid expansion device 140, a heat exchanger 144, e.g. an evaporator, and the temperature sensor 134. Conduit 126 is operable to deliver refrigerant fluid to the conventional refrigerant fluid expansion device 140 and to the heat exchanger 144, respectively. The expansion device 140 includes a remote temperature sensor 140a which is adapted to sense the temperature of refrigerant fluid leaving the heat exchanger 144 by way of a conduit 146. Conduit 146 is commonly known as the suction line leading to the compressor 110 whereby refrigerant fluid in vapor form is compressed and recirculated through the system 100 by way of condenser heat exchanger 116. Heat exchangers 116, 144 may be conventional multiple fin and tube type devices, for example. One who is of skill in the art will understand the functioning of the HVAC heretofore described.

The air purification subsystem 102, within the heat exchanger plenum 150, comprises a filtration media 160 enclosed within frame 162 and adjacent to a light source 164, which may comprise UV lamps or similar UV light sources known to those skilled in the art for use with PCO systems. The filtration media 160 may comprise an air filter layer, a photocatalytic oxidation (PCO) layer, and a barrier layer positioned between said filter layer and PCO layer pleated together. In one embodiment, the PCO layer may comprise a metal media having a photocatalyst coating. In another embodiment, the PCO layer may comprise any other photoreactive metal semiconductor material, including, but not limited to, titanium dioxide ($TiO_2$), zinc oxide (ZO), tin dioxide ($SnO_2$), manganese trioxide ($MnO_3$), tungsten trioxide ($WO_3$), and diron trioxide ($Fe_2O_3$), and various other photoreactive metal coating materials. In some embodiments, the light source 164 may comprise a UV lamp. In a one embodiment, the light source 164 emits photons of a particular wavelength to cause the photons to be absorbed by the PCO media, promoting an electron from the valence band to the conduction band, thus producing a hole in the valence band and adding an electron in the conduction band. The promoted electron reacts with oxygen, and the hole remaining in the valence band reacts with water, forming reactive hydroxyl radicals. When a contaminant adsorbs onto the photocatalyst, the hydroxyl radicals attack and oxidize the contaminants to water, carbon dioxide, and other substances.

Figure 2:
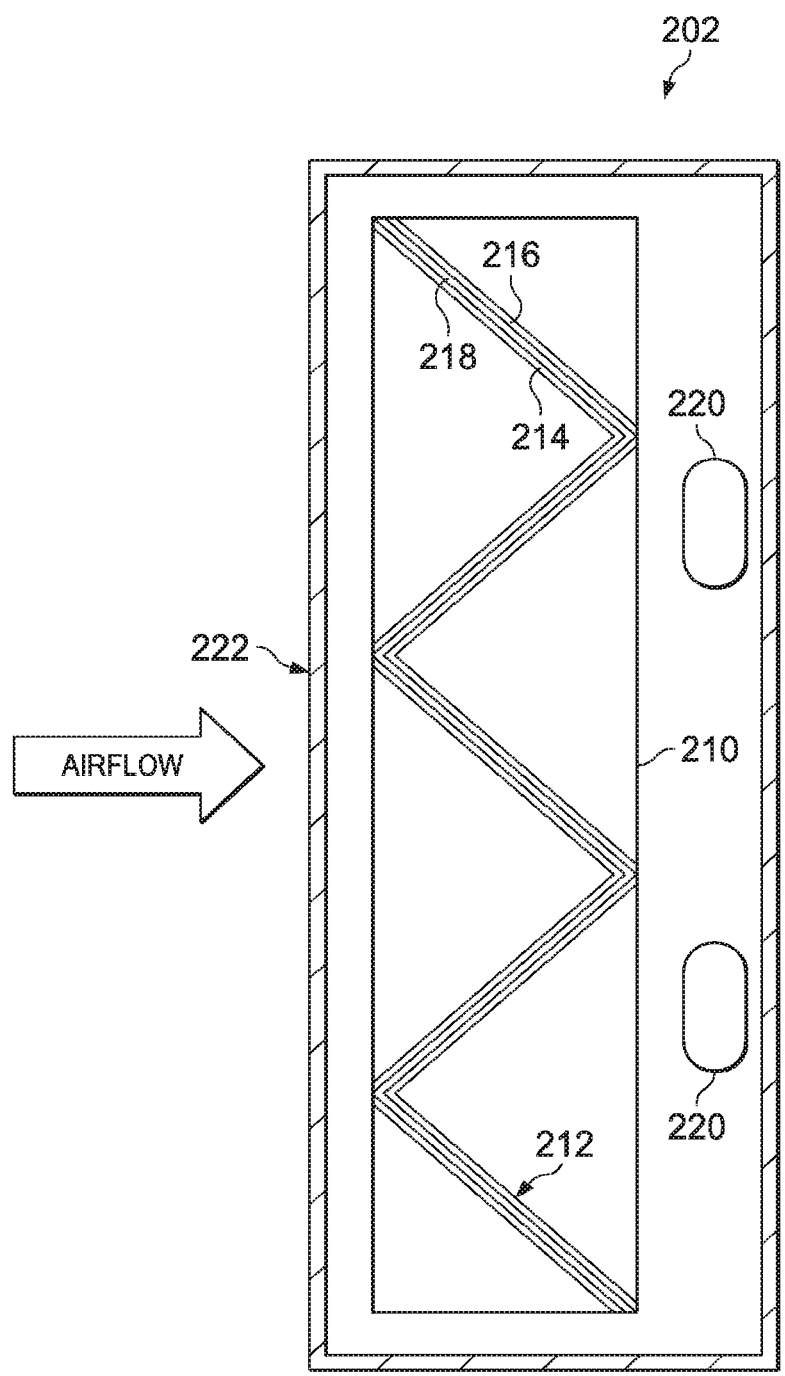
FIG. 2 is a side view of one embodiment of a PCO subsystem according to the present disclosure.

Referring now to FIG. 2, illustrated is shown one embodiment of an air purification system 202 which may be used in the HVAC system 100 of FIG. 1. The air purification system 202 comprises a frame 210 for enclosing filtration media 212. The filtration media 212 comprises an air filter layer 214 having a first and second side. A PCO media 216 of the filtration media 212 comprises a first and second side. A barrier layer 218 may be positioned between the second side of the air filter layer 214 and the first side of the PCO layer 216. Outside of the frame 210, proximal to the second side of PCO layer 216 is a light source 220, which may comprise UV lamps and other similar UV light sources which may be known in the art for use in conjunction with PCO media for removal of air contaminants in an HVAC system. The purification system 202 may be enclosed within an enclosure 222 for placement within an HVAC system, the enclosure 222 comprising a plenum, cabinet, or other suitable enclosing structure for placement within an HVAC system.

The air filter layer 214 may comprise a fibrous membrane filter media comprising polypropylene, polyester, fiberglass, resins, or various other fiber materials used in traditional air filter fabrication such that the filter media 214 may be folded into multiple pleats while enabling uniform air flow through the air filter layer. In one embodiment, the air filter layer 214 may comprise a high efficiency particulate air (HEPA) filter. The PCO layer 216 may comprise a metal media having a photocatalyst coating, including, but not limited to titanium dioxide and any other photo reactive metal semiconductor material for use in air purification systems.

The barrier layer 218 may comprise an independent layer between the air filter layer 214 and PCO layer 216, but also be a laminate which is adhered onto either the second side of the air filter layer 214 or onto the first side of the PCO layer 216 such that the barrier will be a light absorptive or reflective barrier for providing photo catalytic protection for the air filter layer 214. Accordingly, the barrier layer 218 may comprise coated or non-coated organic or inorganic materials such as polyester, glass, metal, or any non-photo-oxidizable, UV protected and stabilized material which may be pleated and or adhered onto the air filter layer 214 or metal PCO layer 216, such that the air filter layer 214 is protected from the UV or photocatalytic rays from the light source 220.

Figure 3C:
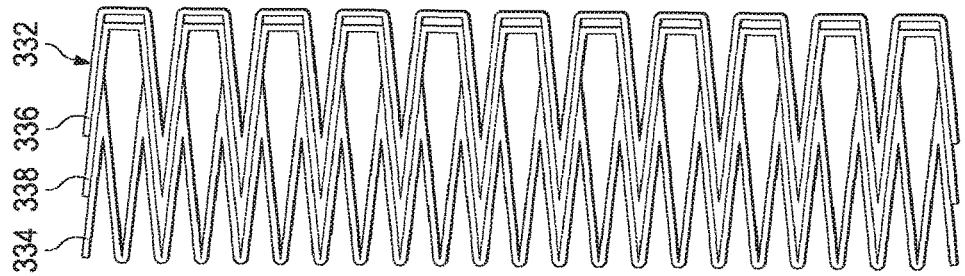
FIG. 3C illustrates yet another embodiment of an air filter/PCO media according to the present disclosure.
Figure 3B:
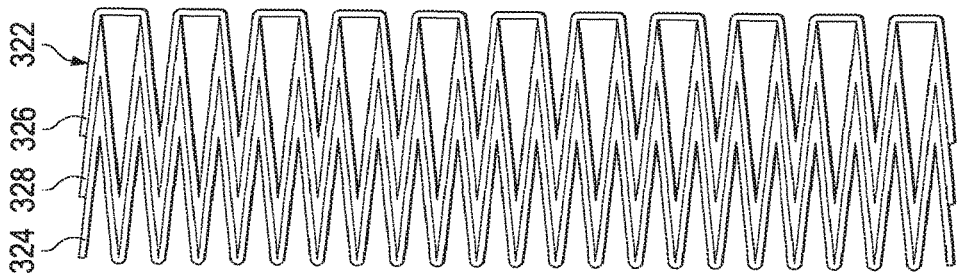
FIG. 3B illustrates another embodiment of an air filter/PCO media according to the present disclosure.
Figure 3A:
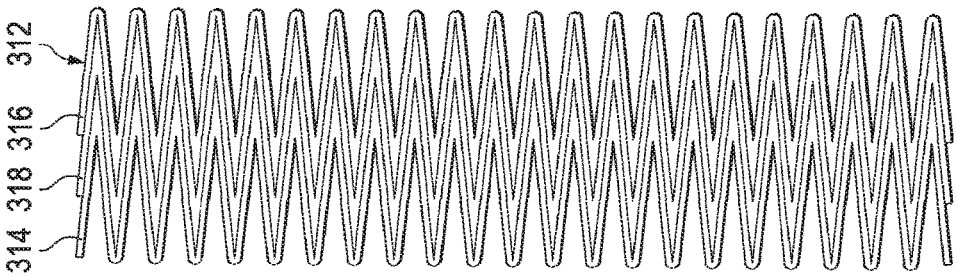
FIG. 3A illustrates one embodiment of an air filter/PCO media according to the present disclosure.

Referring now to FIG. 3A through 3C, there are shown three embodiments of filtration media which may be utilized in the purification system 102 according to the present disclosure. As shown in FIG. 3A, filtration media 312 comprises an air filter layer 314, barrier layer 318, and PCO layer 316 may be coupled altogether into a continuous sheet which is pleated into multiple uniform pleats. As shown in FIG. 3B, filtration media 322 comprises air filter layer 324 and barrier layer 328 coupled together as one continuous sheet and pleated into multiple uniform pleats. PCO layer 326 is displaced adjacent the barrier layer 218, but pleated in a different pattern which is less dense in quantity of pleats than the number of air filter/barrier pleats, such that the PCO may still react with an adjacent light source while enabling uniform airflow through filtration media 322. Referring now to FIG. 3C, there is shown another embodiment of filtration media 332 comprising an air filter layer 334 comprising a continuous sheet pleated into multiple uniform pleats. Adjacent the air filter layer 334 is barrier layer 338 and PCO layer 336 pleated together in a different pleat pattern that is less dense in pleats than the number of pleats of air filter layer 334, such that PCO layer 336 still reacts with an adjacent UV light source while the barrier layer 338 still protects the air filter layer 332. Accordingly, the air filter layer 332, barrier layer 338, and PCO layer 336 may be pleated in various multiple pleating patterns, as long as a uniform airflow is enabled through filtration media 332 in an HVAC system and air filter layer 332 is protected from the adjacent light source.

Figure 4:
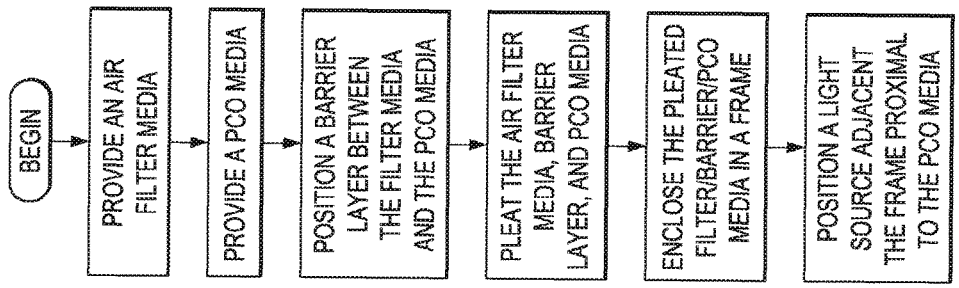
FIG. 4 is a flow diagram of a method of manufacturing a PCO subsystem according to the present disclosure.

Referring now to FIG. 4, there is shown a flow diagram of a method of manufacturing an air purification system according to the present disclosure. The method comprises, inter alia, providing an air filter media having a first side and a second side. A PCO media having a first and second side is provided and a protective barrier is positioned between the second side of the air filter media and the first side of the PCO media. The air filter media, barrier, and PCO media may be pleated together, or in various combinations, into at least one pleating pattern having multiple pleats and enclosing the at least one pleating pattern within a frame. A light source, such as, e.g, a UV lamp, is positioned adjacent the frame proximal to the second side of the PCO media; wherein the frame and light source are positionable within the plenum of a HVAC system. In some embodiments, the barrier layer may be a laminate coated onto the second side of the air filter media. In another embodiment, the barrier layer may be a laminate coated onto the first side of the PCO media.

Although the present disclosure has been described in detail, those skilled in the pertinent art should understand that they can make various changes, substitutions and alterations herein without departing from the spirit and scope of the disclosure in its broadest form.

The invention claimed is:

1. A method for air purification for a heating, ventilation and air condition (HVAC) system, the method comprising:
   providing an air filter media layer, a photocatalytic oxidation (PCO) media layer, and a barrier layer within a frame;
   wherein the barrier layer is positioned between the air filter media layer and the PCO media layer;
   placing the frame comprising the air filter media layer, the barrier layer, and the PCO media layer adjacent a light source that produces ultraviolet (UV) light;
   wherein air flow enters through the air filter media layer and exits through the PCO media layer;
   wherein the PCO media layer and the light source are configured to destroy air contaminates; and
   wherein the barrier layer comprises an independent layer of coated glass that is configured to protect the air filter media layer from the UV light produced by the light source.

2. The method according to claim 1 further comprising pleating the air filter media layer, the barrier layer, and the PCO media layer into at least one pleating pattern.

3. The method according to claim 1, wherein the PCO media layer comprises a photo-reactive metal semiconductor material.

4. The method according to claim 3, wherein the photo-reactive metal semiconductor material comprises titanium dioxide.

5. The method according to claim 1, wherein the air filter media layer is a high-efficiency particulate air (HEPA) filter.

6. The method according to claim 1, wherein the barrier layer possesses light-absorbing capabilities.

7. The method according to claim 1, wherein the barrier layer possesses light-reflecting capabilities.

8. The method according to claim 1, wherein the air filter media layer comprises a fibrous membrane filter.

9. A method of manufacturing an air purification system for use in a plenum comprising a heating, ventilation and air condition (HVAC) system, the method comprising:
   providing an air filter media layer comprising a first side and a second side;
   providing a photocatalytic oxidation (PCO) media layer having a first side and a second side;
   positioning a barrier layer between the second side of the air filter media layer and the first side of the PCO media layer;

pleating the air filter media layer, the barrier layer, and the PCO media layer into at least one pleating pattern;

enclosing the at least one pleating pattern within a frame;

positioning the frame adjacent a light source that produces ultraviolet (UV) light;

placing the frame and the light source within the plenum; and wherein the barrier layer comprises an independent layer of coated glass that is configured to protect the air filter media layer from the UV light produced by the light source.

10. The method according to claim 9, wherein the air filter media layer, the barrier layer, and the PCO media layer are folded together into a uniform multiple pleat pattern.

11. The method according to claim 9, wherein the PCO media layer comprises a photo-reactive metal semiconductor material.

12. The method according to claim 11, wherein the photo-reactive metal semiconductor material comprises titanium dioxide.

13. The method according to claim 9, wherein the air filter media layer is a high-efficiency particulate air (HEPA) filter.

14. The method according to claim 9, wherein the barrier layer possesses light-absorbing capabilities.

15. The method according to claim 9, wherein the barrier layer possesses light-reflecting capabilities.

16. The method according to claim 9, wherein the air filter media layer comprises a fibrous membrane filter.

* * * * *